US005593863A

United States Patent [19]

Eberwine et al.

[11] Patent Number: 5,593,863

[45] Date of Patent: Jan. 14, 1997

[54] ADMINISTRATION OF AN RNA STEM LOOP STRUCTURE TO MODULATE PROTEIN SYNTHESIS

[75] Inventors: James H. Eberwine; Corinne Spencer, both of Philadelphia, Pa.

[73] Assignee: Trustees of the University of Pennsylvania, Philadelphia, Pa.

[21] Appl. No.: 327,393

[22] Filed: Oct. 19, 1994

Related U.S. Application Data

[63] Continuation of Ser. No. 178,600, Jan. 7, 1994, abandoned, which is a continuation of Ser. No. 844,305, Feb. 28, 1992, abandoned.

[51] Int. Cl.[6] .......................... C12P 21/00; C12N 15/67; C07K 14/575; C07K 14/665

[52] U.S. Cl. ...................... 435/69.1; 435/69.4; 435/70.1; 530/399; 935/33; 935/34

[58] Field of Search ................................ 435/69.1, 69.4, 435/70.1, 71.1, 6; 935/33, 34, 35, 36, 37, 38, 39, 44; 530/350, 399

[56] References Cited

U.S. PATENT DOCUMENTS

| | | | |
|---|---|---|---|
| 4,820,639 | 4/1989 | Gehrlu | 435/69.1 |
| 5,021,335 | 6/1991 | Tecott et al. | 435/6 |

OTHER PUBLICATIONS

Bomford et al., "Ferritin Gene Expression in Health and Malignancy," *Pathobiology* 1992, 60(1). 10–18.

Brady et al., "Long–term Antidepressant Administration Alters Corticotropin–Releasing Hormone, Tyrosine Hydroxylase, and Mineralocorticoid Receptor Gene Expression in Rat Brain," *J. Clin. Invest.* 1991, 87(3), 831–837.

Bruhn et al., "Corticotropin–Releasing Factor Regulates Proopiomelancortin Messenger Ribonucleic Acid Levels in vivo," *Neuroendocrinology* 1984, 39, 170–175.

Childs et al., "Use of the Reverse Hemolytic Plaque Assay to Study the Regulation of Anterior Lobe Adrenocorticotropin (ACTH) Secretion by ACTH–Releasing Factor, Arginine Vasopressin, Angiotensin II, and Glucocoritocoids," *Endocrinology* 1987, 120, 439–444.

Clark et al., "Translation Control by the Epstein–Barr Virus Small RNA Eber–1," *Eur. J. Biochem.* 1990, 193(3), 635–641.

Hughes et al., "Effect of IDPN on the Expression of POMC–Derived Peptides in Rat Motoneurones," *Peptides* 1992, 13(5), 1021–1023.

Longley et al., "In Situ Transcription and Detection of CD1a mRNA in Epidermal Cells: an Alternative to Standard In Situ Hybridization Techniques," *J. Inves. Derm.* 1989, 93, 432–435.

Nagai et al., "Interplay of Two Cis–Acting mRNA Regions in Translational Control of $o^{32}$ Synthesis During the Heat Shock Response of *Escherichia coli*,"*Proc. Natl. Acad. Sci. USA* 1991, 88(23), 10515–10519.

Oliveira et al., "Inhibition of Translational Initiation in *Saccharomyces cerevisiae* by Secondary Structure: the Roles of the Stability and Position of Stem–Loops in the mRNA Leader," *Mol. Microbiol.* 1993 9(3), 521–532.

Roberts et al., "Selective Reduction of Proadrenocorticotropin/Endorphin Proteins and Messenger Ribonucleic Acid Activity in Mouse Pituitary Tumor Cells by Glucocorticoids," *Biochemistry* 1979, 28, 4907–4915.

Tecott et al., "In Situ Transcription: Specific Synthesis of Complementary DNA in Fixed Tissue Sections," *Science* 1988, 240, 1661–1664.

Wikstrom et al., "Importance of mRNA Folding and Start Codon Accessibility in the Expression of Genes in a Ribosomal Operon of *Eschericia coli*," *J. Mol. Biol.* 1992 224(4), 949–966.

Young et al., "Specific Inhibition of Protein Kinase A in Granulosa Cells Abolishes Gonadotropin Regulation of the Proopiomelanocortin Promoter," *J. Biol. Chem.* 1991, 266(24), 15839–15844.

Yu et al., "Regulation of int Gene Expression in Bacteriophage P2," *J. Virol.* 1994, 68(7), 4220–4226.

Zanger et al., "In Situ Transcription: a Methodological Study using Proopiomelanocortin Gene Expression in the Rat Pituitary as a Model," *Technique* 1989, 1, 108–117.

Spencer et al J Cell Biol 115(3Pt2) 99A 1991.

Chevrier et al J Biol Chem 263(2) 902–909 1988.

Lawson et al J Biol Chem 261(30) 13979–13989 1986.

Eguchi et al J Mol Biol 220 831–842 1991.

Selby et al Cell 62 769–776 1990.

Roy et al Eur J Biochem 191 647–652 1990.

*Primary Examiner*—David Guzo

*Assistant Examiner*—Nancy J. Degen

*Attorney, Agent, or Firm*—Law offices of Jane Massey Licata

[57] ABSTRACT

A method for modulating synthesis of a selected protein in a cell or tissue by contacting the cell or tissue with at least a portion of a mRNA stem loop structure are provided. Compositions containing a mRNA stem loop structure are also provided.

5 Claims, No Drawings

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 112
( B ) TYPE: Nucleic acid
( C ) STRANDEDNESS: Single
( D ) TOPOLOGY: Linear ( i v ) ANTI-SENSE: No ( x i ) SEQUENCE DESCRIPTION: SEQ ID NO: 1:

```
GACCTCCATA GACGTGTGGA GCTGGTGCCT GGAGAGCAGC CAGTGCCAGG   50

ACCTCACCAC GGAAAGCAAC CTGCTGGCTT GCATCCGGGC CTGCAGACTC  100

GACCTCTCGG CG                                           112
```

ADMINISTRATION OF AN RNA STEM LOOP STRUCTURE TO MODULATE PROTEIN SYNTHESIS

This application is a continuation of application Ser. No. 08/178,600, filed Jan. 7, 1994, now abandoned, which is a file wrapper continuation of application Ser. No. 07/844,305, filed Feb. 28, 1992, now abandoned.

BACKGROUND OF THE INVENTION

The level of expression of a protein can be affected by several different mechanisms following transcription initiation. For example, the level of expression of the Int gene of bacteriophage P2 has been shown to be controlled by three different mechanisms (Yu et al., *J. Virol.* 1994, 68(7), 4220–6). First, a partial transcription termination signal located between the Int and C genes reduces the transcriptional readthrough by about 30%. Second, the ribosome binding site and AUG codon of the Int gene are located in a putative stem loop structure which may inhibit the initiation of translation. The third control of int expression in P2 seems to be posttranscription autoregulation wherein the binding site of the int protein on Int gene mRNA is shown to extend into the ribosome binding site of Int, supporting a competitive binding theory between Int and ribosomes. It has been recognized, however, that translation is a very important control step in gene expression.

It is believed that at least one of the functions of the secondary and tertiary structure of RNA is the control of translation. Mutations which prevent the formation of secondary structures such as stem loops have been shown to increase expression of a protein up to 20 fold (Wikstrom et al., *J. Mol Biol.* 1992 224(4), 949–966). In addition, insertion of stem loop structures into a gene expression system such as *Saccharomyces cerevisiae* has been shown to inhibit translation up to 89% (Oliveira et al. *Mol. Microbiol.* 1993 9(3), 521–532).

One mechanism by which translational control is thought to occur is by regulation of ribosome movement down the mRNA by the specific binding of cytosolic proteins to the RNA structure. It is believed that for many proteins, this binding occurs in the secondary structure such as a stem loop structure. For example, intracellular iron can be stored in the protein shell of ferritin to protect the cell against the toxic action of the iron. In response to increased iron, some ferritin subunits are synthesized using translation and transcriptional mechanisms. Translational control has been shown to involve a unique stem loop structure in the 5' untranslated region of the subunit messengers (Bomford et al. *Pathobiology* 1992, 60(1), 10–18). When the iron level is low, a protein binds to this stem loop structure and prevents translation. When intracellular iron levels rise, the repressor protein is discharged and the large population of messengers begins to translate.

It has also been shown that the Epstein-Barr virus small RNA species, EBER-1, controls protein synthesis in a similar fashion (Clark et al. *Eur. J. Biochem.* 1990, 193(3), 635–641). It was found that EBER-1 prevents inhibition of protein synthesis caused by low concentrations of synthetic double-stranded RNA. This effect was eliminated by disruption of the secondary structure of EBER-1. Thus, it was suggested that the ability of EBER-1 to regulate protein synthesis is dependent upon the secondary structure of the RNA molecule.

The transient disruption of the secondary RNA structure has also been implicated as a primary step in the expression of proteins due to heat shock (Nagai et al. *Proc. Natl. Acad. Sci. USA* 1991, 88(23), 10515–9).

It has now been found that administration of at least a portion of a stem loop structure of an mRNA to a cell or tissue can modulate the synthesis of a selected protein in the cell or tissue.

SUMMARY OF THE INVENTION

An object of the present invention is to provide a method for modulating protein synthesis in a cell or tissue which comprises contacting a cell or tissue with an effective amount of an mRNA stem loop structure so that synthesis of the protein is modulated. Compositions comprising an mRNA stem loop structure are also provided.

DETAILED DESCRIPTION OF THE INVENTION

The secondary structure of the mRNA caused by intramolecular base pairing, referred to as the stem loop structure, is an important factor in the initiation of protein synthesis. Stem-loop structures (intramolecular base paired sequences) are believed to inhibit the translation of mRNA because of the steric hindrance of proteins bound to the loop. Administering a molecule which is capable of binding to a mRNA stem loop structure alters protein synthesis. It has now been found that administration of at least a portion of an mRNA stem loop structure can modulate protein synthesis in a cell or tissue.

For example, it has now been found that pro-opiomelanocortin synthesis in a cell or tissue is decreased by administering at least a portion of a mRNA stem loop structure. Pro-opiomelanocortin (POMC) is the precursor for melanotropic, corticotropic and opioid peptides such as alpha-melanocyte-stimulating hormone, ACTH, and other related peptides. These POMC-derived peptides are stored in secretory vesicles and released upon stimulation with specific seratogues. POMC-derived peptides are mediators in a number of extremely important biological responses.

For example, ACTH secreted from the pituitary gland controls adrenocortical secretions. Adrenocortical secretions allow the body to adapt to stress of all kinds. Inadequate secretions of ACTH from the pituitary gland result in adrenal insufficiencies causing Addison's disease. Clinical manifestations of this disease include muscular weakness, anorexia, gastrointestinal symptoms, fatigue, emaciation, generalized dark pigmentation of the skin, hypotension, low blood sugar, low serum sodium and high serum potassium. Excessive secretions of ACTH can result in overproduction of the adrenal cortical hormone causing Cushing's disease. Growth arrest, obesity, and musculoskeletal changes are manifestation of this disease.

POMC-derived peptides have also been recognized as potent immunomodulatory mediators. They have been found not only in the pituitary but also in the epidermis suggesting that such peptides have a major impact on the skin's immune system. In addition, it has been suggested that POMC-derived peptides may be part of the regenerative repertoire of the damaged motoneurone (Hughes et al., *Peptides* 1992, 13(5), 1021–3).

The gonadotropins, follicle stimulating hormone, luteinizing hormone and human chorionic gonadotropin, and beta-adrenergic agonists have been shown to stimulate expression of POMC in ovarian granulosa cells (Young et al., *J. Biol. Chem.* 1991, 266(24), 15839–44). In contrast, therapeutic agents such as imipramine, a prototypic tricyclic antidepressant utilized in the treatment of major depressions (Brady et al., *J. Clin. Invest.* 1991, 87(3), 831–7), and dexamethasone, a synthetic adrenocortical steroid used as an anti-inflammatory agent (Wang et al., *Endocrinology* 1991, 128(3), 1345–51), decrease POMC mRNA levels. However, neither these stimulators nor inhibitors of POMC are specific to POMC alone. Thus, none of these agents serve as adequate therapeutic agents to specifically target diseases manifested by POMC and POMC-derived peptides.

Tissue and cell-specific regulation of the POMC gene is well recognized. Individual cells contain varying amounts of POMC mRNA secrete disparate amounts of hormone [Childs, G. V. et al., *Endocrinology* 1987, 120, 439–445]. The existence of populations of cells containing distinct POMC mRNA structures suggests that different cells may respond differentially to hormonal challenges, i.e., those cells containing mRNA in an "easily" translatable conformational state may respond more rapidly than other POMC containing cells with mRNA in a different structural state. Such a result would have implication for acute versus longer term effects of modulators of POMC expression including physiological modulators such as stress.

Administration of an mRNA stem loop structure of POMC has now been shown to increase the synthesis of POMC in a cell or tissue. Thus, administration of an mRNA stem loop structure can be used in the treatment of conditions related to POMC-derived peptides. In a preferred embodiment, the mRNA stem loop structure to be administered comprises SEQ ID NO: 1.

In situ transcription (IST), a technique originally devised to decrease the exposure time for detection of mRNAs in situ, is used to determine secondary structure of mRNA [Tecott, L. et al., *Science.* 1988, 240, 1661–1664; Longley, J., J. *Inves. Derm.* 1989, 93, 432–435; and U.S. Pat. No. 5,021,335]. In IST, oligonucleotides are hybridized to mRNA in a tissue section, as is done with in situ hybridization, and reverse transcriptase and radiolabeled nucleotides are then added, resulting in the synthesis of cDNA using the oligonucleotide as a primer. This in situ reverse transcription copies endogenous mRNA into cDNA while preserving the anatomical distribution of the cDNA transcripts. The in situ transcribed radiolabeled cDNAs can be removed from the tissue section by alkaline denaturation of mRNA-cDNA hybrids and be visualized by autoradiography after they have been electrophoresed on denaturing DNA sequencing gels. The banding pattern is characteristic of changes that occur resulting from translational control of mRNAs.

Experiments were designed to confirm the existence of the stem-loop structure in situ. It has been observed that reverse transcriptase does not melt "strongly" base-paired sequences. Therefore, it was predicted that the IST pattern through a predicted stem loop region would be distinctive, reflecting the presence of a structure that inhibits the activity of reverse transcriptase. In these experiments, the oligonucleotide P2, which is complementary to a region approximately 30 bases away from a region of the POMC mRNA which is predicted by Gibbs free energy calculations to contain a stable (about 45 kCal) stem-loop structure, was selected for priming.

The banding pattern from rat pituitary sections showed a single-base ladder that decreased in intensity for 11 bases and then increased again. This decreased intensity in the banding pattern corresponds to the site at which the loop of the stem-loop structure would exist. The low molecular weight single base ladder corresponds to the 3'-end of the stem-loop structure. Immediately after the 11 base decrease in intensity there is a high molecular weight single base ladder which corresponds to the 5'-end of the stem. This banding pattern indicates that the stem-loop structure does exist in situ. Its existence is also supported by the fact that, upon overexposure of the autoradiogram, the single base pattern reverted to the IST banding pattern of the POMC mRNA 18 bases away from the presumed 5'-end of the predicted stem-loop structure. In addition, autoradiographic intensity of the tissue section after IST for the primer P3 always appears weaker than either P1 or P2. Primer P3 was synthesized so that it would hybridize to the 3'-portion of the presumed stem-loop structure. The lower signal indicates that hybridization of the oligonucleotide was hindered because the priming site was already base-paired with the 5'-end of the stem-loop structure in some of the POMC mRNAs.

When primer extension was performed on rat pituitary mRNA in solution and then electrophoresed on a DNA sequencing gel, a smear of termination sites appeared. Most bands did not correspond to the bands observed from the POMC mRNA derived from tissue sections. This disparity in banding pattern indicates that POMC IST-generated cDNA results from an interaction of POMC mRNA in situ with cellular structures. Specific termination of cDNA synthesis could be due to steric interference, perhaps through an interaction of mRNA in situ, with itself or with other molecules that inhibited the procession of reverse transcriptase in the assay system.

Agents which enhance POMC production by translation are believed to increase loading of ribosomes on POMC mRNA. This increase would result in a shift in the relative intensities of the IST banding pattern such that the longer cDNAs (high molecular weight bands) are lower in abundance than are the shorter cDNA (low molecular weight bands). Treatment of POMC-producing cells with the POMC-peptide secretagogue, forskolin, lowered the ratio of high-molecular-weight to low molecular weight IST bands compared to control. The polysome profile showed that forskolin increased the amount of POMC mRNA in the polysome fraction. Dexamethasone, which decreases POMC synthesis, caused a reversal of the ratio of the autoradiographic intensity of cDNA bands, with the intensity of longer cDNAs increasing relative to the shorter cDNAs (autoradiographic ratio=3.1). The polysome profile showed that dexamethasone decreased the amount of POMC mRNA in the polysome fraction. NaF decreases POMC-peptide secretion and has been reported to inhibit ribosome binding to mRNA. NaF treatment of AtT20 cells also decreased the number of POMC mRNAs in the polysome fractions of the gradient and increased the intensity of the high molecular weight IST-derived cDNA bands compared to the low molecular weight bands within a gel lane. Densitometric examination of the integrated areas of the autoradiographic bands showed that the high to low molecular weight band (arbitrary midpoint on the gel with the bands above the midpoint being high molecular weight and the bands below the midpoint being low molecular weight bands) ratio changes with pharmacological manipulation. The high to low band molecular weight ratios were calculated by determining the total intensity above the midpoint divided by the total intensity below the midpoint. Comparisons between the different pharmacological states were made by dividing the experimental ratio of band intensities by the control ratio. The ratio increased with NaF treatment (autoradiographic ratio=1.42). This confirms that there is an increase in the molar amounts of higher molecular weight bands relative to lower molecular weight bands with NaF treatment. These data indicate that longer IST transcripts increase in abundance relative to shorter transcripts when there are fewer ribosomes associated with the POMC mRNA.

The ability of AtT20 cytosol to bind specifically to the region of RNA which is predicted to exist as a stem-loop structure indicates that this unique portion of the POMC mRNA is subject to regulatory factors which can modulate the translatability into POMC peptides.

The presence of a specific banding pattern after reverse transcription of POMC mRNA in situ indicates that the enzyme activity terminates at specific sites along the length of the mRNA. These termination sites are sequence-dependent, as demonstrated by the correlation of the banding pattern with the POMC sequence for each of the oligonucleotides used in these experiments. The shift in the ratio of autoradiographic intensities of the higher molecular weight bands relative to the lower molecular weight bands can be interpreted in two ways. First, trivial explanations for termination, including limiting amounts of substrate, fixation conditions, RNA degradation and method of transcript removal, have been tested and eliminated. Second, the termination sites may occur because the sequence surrounding the termination site is involved in forming secondary or tertiary structure that reverse transcriptase has difficulty traversing.

In the present invention methods are provided for modulating synthesis of a selected protein in a cell or tissue capable of expressing the selected protein by contacting the cell or tissue with an effective amount of at least a portion of an mRNA stem loop. By "modulating" it is meant to alter, either by increasing or decreasing, the amount of a selected protein synthesized by a cell or tissue. By "effective amount" it is meant a concentration of the mRNA stem loop structure or portion thereof which, when administered to cell or tissue, results in an alteration in the amount of a selected protein synthesized by the cell or tissue. The stem loop structure or portion thereof to be administered must correspond to a portion of the stem loop structure of mRNA encoding the selected protein. By "at least a portion of" it is meant a sequence of ribonucleic acids of sufficient length and similarity to the stem loop structure of the mRNA encoding the protein such that, upon administration of this sequence to a cell or tissue, normal translational control of the mRNA is interfered with. This alteration in normal translation control can be measured by either an increase or decrease in the amount of the selected protein synthesized by the cell or tissue. For example, if the selected protein is POMC, it is preferred that the stem loop structure to be administered comprises SEQ ID NO: 1. SEQ ID NO: 1 corresponds to a portion of the stem loop structure of the mRNA encoding POMC. Administration of a composition comprising SEQ ID NO: 1 to a cell or tissue capable of synthesizing POMC, such as AtT20 cells, results in an increase in POMC synthesis. The administration of compositions comprising a stem loop structure of an mRNA to a cell or tissue can be performed routinely by those of skill in the art. Agents such as lipofectins are used routinely by those of skill in the art to transfer foreign RNA into a host cell or tissue. Such agents can also be used in the present invention.

The production and isolation of selected proteins from host cells is performed routinely by those of skill in the art. Proteins produced, isolated and purified from host cells have been found to be useful in a variety of applications including, but certainly not limited to, therapeutic agents and diagnostics agents. For example, the protein endothelin is a potent vasoconstrictory agent and antihypotensive useful in the treatment of shock and esophageal and gastric hemorrhage. Interferon has been demonstrated to have potent antiviral activity. Bovine growth hormone and other biologically active polypeptides also provide valuable diagnostic reagents and therapeutics. The method of the present invention can be used to modulate synthesis of selected proteins in these host cell systems. Administration of a composition comprising at least a portion of an mRNA stem loop structure corresponding to the stem loop structure of the mRNA encoding the selected protein can increase the synthesis of the selected protein. Thus, use of the present method and composition, which enhances the protein synthesis, results in higher yield of the selected protein. The method and compositions of the present invention can also be used in the treatment of diseases resulting from a decreased synthesis of a protein.

The following nonlimiting examples are provided to further illustrate the present invention.

EXAMPLES

EXAMPLE 1

Cell Culture

AtT20 cells, a homogeneous line of POMC-producing cells, were grown on poly-lysine coated glass cover slips in DelBecco's modified Eagle's medium (GIBCO, Grand Island, N.Y.) containing 4.5 g/l glucose, penicillin, streptomycin and 15% fetal bovine serum at 37° C. with 5% $CO_2$. Initial density was $5\times10^5$ cells per well in 24-well multi-well plates. Cells were grown for 48 hours, reaching a cellular density of approximately 70% confluency. Medium was aspirated and replaced with fresh medium containing NaF (10 mM) or dexamethasone (1 μM) for 1 hour, or forskolin (10 μM) for 4 hours. After treatment, cells were washed twice with phosphate buffered saline (PBS), fixed for 20 minutes in 3% neutral buffered paraformaldehyde, washed with 2×SSC, and then stored in 70% ethanol at 4° C.

EXAMPLE 2

Tissue Preparation

Adult male Sprague-Dawley rats were used for analysis of IST-banding patterns in vivo. Adrenalectomy was performed under ether anaesthesia, and the rats were allowed to recuperate for 2 weeks. The rats were maintained on 0.7% saline in the drinking water. Dexamethasone (100 μg/kg) was administered daily for three days (at 2:00 p.m.) via intraperitoneal injection. The rats were killed by decapitation, and the pituitary glands were removed, quick-frozen in Cryoquick (International Equipment Co., Needham Heights, Mass.) and stored at −70° C. until sectioning.

For sectioning, the pituitaries were embedded in OCT embedding compound (Miles, Inc., Elkhart, Ind.), sectioned with a cryostat at −14° C., and thaw-mounted on gelatin-coated microscope slides. These slides were washed in PBS, dehydrated through graded ethanol washes, and stored at −70° C. until used for IST.

EXAMPLE 3

Oligonucleotide Probes

Oligonucleotide probes complementary to portions of the POMC mRNA were synthesized on a Biosearch Model 8600 DNA synthesizer (Milligon Biosearch, Burlington, Mass.). These oligonucleotides were 5'-end-labelled with polynucleotides kinase (Boehringer-Mannheim) and $\gamma^{32}$P-ATP (6000

Ci/mM, New England Nuclear) to a specific activity of about $5\times10^8$ cpm/μg.

Cover slips and pituitary tissue sections were hybridized with $1.8\times10^5$ cpm/100 μl of probe in 1×hybridization buffer consisting of 4×10×SSC (0.15M sodium acetate pH 7.0, 1.5M sodium chloride) in 40% formamide and incubated at room temperature for 4 hours. The sections were then washed in 2×SSC at room temperature for 30 minutes followed by two 0.5×SSC at room temperature for two hours each. The sections were then rinsed briefly in distilled water.

Reverse transcription was performed by addition of 150 μl of reverse transcription buffer (50 mM Tris pH 8.3; 6 mM $MgCl_2$; 100 mM KCl; 7.5 mM dithiothreitol (DTT); 120 U/ml RNAsin (RNAase inhibitor available commercially from Life Technologies, Inc., Gaithersburg, Md.); 250 μM dNTPs; 600 U/ml of Avian myeloblastosis virus (AMV) reverse transcriptase (Seikagaku, Bethesda, Md.) and incubation at 37° C. for one hour. The samples were washed in 2×SSC at room temperature for 30 minutes and then in 0.5×SSC at 40° C. for 6 hours.

EXAMPLE 4 cDNA Transcript Isolation and Gel Analysis

Cellular material was removed from cover slips and slides with a minimum volume of 1N NaOH. Material from 3–8 cover slips was pooled for each treatment, while two tissue sections were pooled for each treatment. The solution containing the transcripts was neutralized with 1N HCl. Volume was brought to 400 μl with water, NaCl was added to 0.5M, and the solution was extracted in phenol-chloroform twice and precipitated with ethanol using 10 μg of glycogen as a carrier. Alternatively, transcripts were removed by dispersion in 0.1N NaOH/1% SDS, followed by addition of 0.75 volumes of 5M potassium acetate, centrifugation at 4° C. for 5 min and ethanol precipitation of the cDNAs.

Gel analysis of the cDNA transcripts was performed on 6% polyacrylamide/7M urea gels. Gels were transferred to 3 MM chromatography grade filter paper, vacuum dried and then exposed for 2–7 days with an intensifying screen at −70° C.

EXAMPLE 5

In Situ Transcription

When POMC mRNA from rat pituitary or mouse AtT20 cells were transcribed in situ using oligonucleotide P1, two distinct transcript banding patterns were observed on DNA sequencing gels. The specific activity of each band is the same because the transcript was labeled once at the 5'-end of the oligonucleotide primer. Thus, different intensities of the cDNA bands indicate different molar amounts of cDNA. Comparison of the mRNA base sequence with the IST bands revealed that the bands correspond primarily with the presence of G residues. The banding pattern is not generated by alkaline hydrolysis of cDNA because several different denaturing agents, including KOH, NaOH, guanidinium hydrochloride, and guanidinium isothiocyanate have been used to remove cDNA from the tissue sections and yield identical banding patterns (Zanger, I. et al., *Technique* 1989, 1, 108–117). To ensure that these bands did not result from an artifact due to cross-linking of the mRNA to other molecules by the paraformaldehyde treatment of the section, unfixed rat pituitary tissue was subjected to the identical treatment, and the same banding pattern as was observed in the fixed tissue was observed.

Treatment of AtT20 cells with the POMC-peptide secretagogue, forskolin, lowered the ratio of high-molecular-weight to low molecular weight IST bands compared to control. The polysome profile showed that forskolin increased the amount of POMC mRNA in the polysome fraction. Dexamethasone, which decreases POMC synthesis, caused a reversal of the ratio of the autoradiographic intensity of cDNA bands, with the intensity of longer cDNAs increasing relative to the shorter cDNAs (autoradiographic ratio=3.1). The polysome profile showed that dexamethasone decreased the amount of POMC mRNA in the polysome fraction. The limited time-course of these manipulations was too short to elicit changes in POMC mRNA levels.

EXAMPLE 6

POMC IST Banding Pattern in the Rat Pituitary

Modulation of alterations in band intensity resulting from the position of the oligonucleotide primer within POMC mRNA was examined. Regions of POMC mRNA predicted by Gibbs free energy calculations to be involved in forming mRNA secondary structure were studied. An IST-signal in the tissue sections using all four oligonucleotides as primers for in situ cDNA synthesis was generated. P1, P2 and P4 gave approximately the same autoradiographic intensity in the intermediate lobe of the pituitary, while P3 gave a signal which was far less intense.

The IST-cDNA banding patterns in pituitaries derived from intact and adrenalectomized rats are quite distinguishable. Adrenalectomy, which increases POMC protein synthesis and secretion [Roberts, J. et al., *Biochemistry* 1979, 28, 4907–4915; Bruhn, T. et al., *Neuroendocrinology* 1984, 39, 170–175] caused a shift of band intensities, such that the higher molecular weight bands were relatively less abundant than the lower molecular weight bands in all three oligonucleotide primers.

EXAMPLE 7

Stem-Loop Structure of POMC mRNA in Situ

The ability of AtT20 cytoplasmic proteins to bind specifically to the RNA structure was assessed using an RNA gel shift assay. A 196 base region of the POMC cDNA containing the putative stem-loop structure was subcloned into the Bluescript cRNA vector (Stratagene, La Jolla, Calif.). Radiolabeled sense cRNA was synthesized and mixed with S100 cytoplasmic extract from AtT20 cells. The mixture was electrophoresed on a 4% polyacrylamide gel. The mobility of free cRNA upon binding of protein extracts to the mRNA was found to shift dramatically. Four bands appeared upon binding of the protein to the radiolabeled cRNA. As a control, cRNAs made to other regions of the POMC precursor which are not involved with the stem-loop structure did not alter the banding pattern when they were added with the specific cRNA. Alone, these non-specific RNAs did not produce this specific gel shift experiments indicating that AtT20 cells contain cytoplasmic proteins which specifically bind to the putative stem-loop structure in POMC mRNA.

What is claimed is:

1. A method of increasing synthesis of a selected protein in a cell or tissue capable of expressing the selected protein comprising contacting the cell or tissue with an effective amount of at least a portion of an mRNA stem loop structure corresponding to the stem loop structure of mRNA encoding the selected protein so that the synthesis of the selected protein is increased.

2. The method of claim 1 wherein the protein is proopiomelanocortin.

3. The method of claim 2 wherein the mRNA stem loop structure comprises SEQ ID NO: 1.

4. A composition for increasing synthesis of a selected protein in a cell or tissue comprising at least a portion of an mRNA stem loop structure corresponding to the stem loop structure of mRNA encoding the selected protein, and an agent to transfer RNA into the cell.

5. The composition of claim 4 wherein the mRNA stem loop structure comprises SEQ ID NO: 1.

* * * * *

UNITED STATES PATENT AND TRADEMARK OFFICE

CERTIFICATE OF CORRECTION

PATENT NO. : 5,593,863
DATED : January 14, 1997
INVENTOR(S) : Eberwine, et al.

It is certified that error appears in the above-indentified patent and that said Letters Patent is hereby corrected as shown below:

At col 1, line 9, please insert therefor --This invention was supported in part by funds from the U.S. Government (NIH Grant DK36054) and the U.S. Government may therefore have certain rights in the invention--.

Signed and Sealed this

Twelfth Day of October, 1999

Attest:

Q. TODD DICKINSON

*Attesting Officer* *Acting Commissioner of Patents and Trademarks*